United States Patent [19]

Barth

[11] 4,132,770

[45] Jan. 2, 1979

[54] ORAL PRODUCT

[75] Inventor: Jordan Barth, East Brunswick, N.J.

[73] Assignee: Colgate Palmolive Company, New York, N.Y.

[21] Appl. No.: 857,478

[22] Filed: Dec. 5, 1977

Related U.S. Application Data

[63] Continuation of Ser. No. 701,489, Jun. 30, 1976, abandoned.

[51] Int. Cl.$^2$ .............................................. A61K 7/16
[52] U.S. Cl. ........................................ 424/49; 424/58
[58] Field of Search .................................. 424/49–58

[56] References Cited

U.S. PATENT DOCUMENTS

| | | | |
|---|---|---|---|
| 3,518,343 | 6/1970 | Welsh et al. | 424/44 |
| 3,729,553 | 4/1973 | Gold et al. | 424/44 |
| 3,876,759 | 4/1975 | Pensak | 424/58 |

OTHER PUBLICATIONS

National Formulary N.F. VII (1942), A. Ph. A. Wash., D. C., pp. 263–264, "Solution of Soda and Mint".
Soine et al., "Rogers Inorganic Pharmaceutical Chemistry", 6th ed. (1957) Henry Kimpton, London, pp. 201–208, "Sodium Bicarbonate".
Osol et al., Dispensatory of the U.S. 25th Ed. (1955), J. P. Lippincott, Phila, Pa., pp. 1253–1255, "Sodium Bicarbonate; Soda and Mint Solution".
Jacobs Am. Perf. & Essential Oil Review 61: 469, 471 Jun. 1953, "Flavoring Mouth Washes".
Balsam et al., Cosmetics Science & Technology, 2nd ed. (1975), vol. 1, pp. 533–563, Mouthwashes, vol. 3, pp. 539, 554–558, 563, 567, "Color in Cosmetics".

*Primary Examiner*—Shep K. Rose
*Attorney, Agent, or Firm*—Murray M. Grill; Herbert S. Sylvester

[57] ABSTRACT

There is disclosed an aqueous oral product including sodium bicarbonate in solution, a flavor oil where desired, and at least one emulsifying agent for said flavor oil; and a dye if color is required; there may optionally be included a cosmetic alcohol, a humectant and sweetening agents. The product is especially suitable as a mouthwash and rinse.

7 Claims, No Drawings

ORAL PRODUCT

This is a continuation, of application Ser. No. 701,489, filed June 30, 1976, now abandoned.

This invention relates to a liquid mouthwash formulation, more particularly, to a mouthwash having the stimulating and refreshing taste of sodium bicarbonate. More specifically, the invention provides for an aqueous mouthwash containing an appreciable level of sodium bicarbonate in solution as the essential active ingredient, a suitable flavor, and emulsifier therefor where desired and optionally a color stable dye.

Baking soda has for many years been employed in various fields and is a common household ingredient. In past years, its use in the area of oral hygiene has been proposed, but has not received much acceptance, generally because of formulation problems encountered in providing for a storage stable product.

The development of a practical and effective baking soda mouthwash capable of consumer acceptability presents many special considerations. Among the factors which are to be considered are the unique character of baking soda chemically, physically and cosmetically, especially when considered as a mouthwash ingredient. It is extremely salt to the taste; and taste is one of the more important factors in the purchase and use of an oral product. Furthermore, baking soda presents solubility considerations with respect to the two major liquid components of a mouthwash; for example, it is substantially alcohol insoluble and comparatively insoluble in alcohol-water systems and under certain conditions, tends to release carbon dioxide in an aqueous system. Other factors in the formulation of a suitable product include the over-all taste and visual appearance of the final product, and its stability combined with special care in manufacture, etc.

In accordance with various aspects of this invention, it is now possible to prepare a mouthwash, having a high level of solubilized baking soda which mouthwash is effective is promoting hygiene in the oral cavity and has consumer desirability and acceptability. Such a product will have acceptable and desirable characteristics so as to have a beneficial effect upon parts of the dentition (which may include the teeth and its surrounding or adjacent elements or structures including plaque, calculus, gingiva, mucous membranes, saliva, etc.). In particular, it tends to leave one with a desirably clean mouth feel effect. The product can be formulated so it is substantially stable upon aging or storage without significant release of carbon dioxide bubbles or other forms of undesirable reaction.

To obtain consumer acceptance, a mouthwash formulation should have an attractive and consistent color and a pleasant flavor. The use of certain specific flavoring and color ingredients in the instant product has created stability and/or compatibility problems and therefore care must be taken in the selection of the proper components and the amounts thereof so as to produce a stable product.

In a baking soda mouthwash, color has been found to be a particularly troublesome problem due to the limited number of color stable dyes and due to the inherent alkalinity of the mouthwash which is believed to exert an adverse effect upon the stability of the dye. The foregoing is manifested by fading of the color upon moderate aging of the mouthwash. A further problem is that under the alkaline conditions prevalent in a baking soda mouthwash, color has been found to be affected by light; the color stability of the mouthwash is therefore subject to the adverse effects of two mechanisms, viz, pH and light.

Ordinarily, most conventional mouthwashes contain approximately the same quantity of dye therein, irrespective of the particular type of mouthwash being formulated. These same dyes, however, when employed at these same conventional levels in this formulation, behave in an unusual fashion, i.e., they fade. This heretofore generally acceptable and proven level of color for mouthwashes has, however, been found to be seriously affected by light and the chemistry of the instant formulation, imparted in part, due to the presence of baking soda. It has been unexpectedly found that a particular select group of dyes, as further defined hereinafter, when used at the instant levels of concentration, either arrest the aforesaid adverse mechanisms or prevent the initiation thereof.

Flavor also plays an important role in the instant invention. It has repeatedly been stated that taste and flavor are perhaps the most important single aspects with respect to the consumer acceptance of a mouthwash formulation. The selection of acceptable flavoring ingredients is therefore of paramount importance in the formulation of a mouthwash. It has oftentimes been stated that the foregoing is both an art as well as a science. It is an art in the sense that it requires the blending of the various components with the flavoring agents such that in the final composition the flavor is stable. The foregoing has presented particular difficulties in incorporating flavoring agents in this mouthwash formulation inasmuch as the former must be compatible with the latter and remain essentially unchanged over the shelf life of the product. Again, the very nature of the baking soda is believed to be the causative agent.

The sensation of flavor is believed to be made up of taste received by the taste buds on the tongue, odors picked up by the olfactory mucosa of the nose as sensations, such as burning, cooling and astringency transmitted through the tactile nerve endings in the mouth. Flavor sensation is made up essentially of four basic tastes, sweet, sour, bitter and salty, which are registered by the taste buds on the tongue. Bitter flavors are detected by the back of the tongue, sweet at the tip, sour along the sides from midway to the back of the tongue and saltiness is detected more or less equally along the entire tongue.

A bicarbonate of soda mouthwash is inherently salty and the salt sensation is therefore detected by the taste buds along the entire tongue, registering an almost immediately perceptible strong sensation. It is therefore crucial that the formulator effectively mask or subdue the rapid and strong salt taste that is manifested by the instant product so as to render the same cosmetically acceptable. One must, therefore, partially mute the salty sensation or substantially overcome it.

The prior art relating to baking soda mouthwashes, generally has taught a level of only about 2% baking soda or less. The foregoing is believed not to be coincidence, but rather a direct result of the difficulties in formulating the product.

Generally speaking, the products of the prior art disregarded flavor, color and stability by maintaining a low level of baking soda in the product. The instant invention has, however, overcome many of the prior art difficulties. As a matter of fact, herein, a substantially greater level of baking soda has been incorporated in the formulation, i.e., between about 3 and 9% baking soda. With respect to baking soda, this is a significantly higher level and an even greater challenge to the formulator in providing for a cosmetically effective as well as storage stable product.

All flavor oils are not operative to accomplish this result, firstly due to the deployment of the various taste receptor buds along the tongue, and secondly, even an increased concentration of most flavor oils fails to effectively compete with the salt sensation - salt receptor mechanism.

It has surprisingly been found, however, that certain select flavors from among the vast majority of available flavor oils when employed at certain concentrations will overcome this problem.

Another problem encountered in formulating a mouthwash product containing baking soda and flavor relates to the use of a suitable emulsifier for the aforesaid flavor oil, with the attendant problems discussed above relating to the flavor per se.

Emulsifiers are conventionally employed in mouthwash formulations and they are generally of the nonionic type, though anionic emulsifiers should also be effective. Either type is customarily employed at levels of about 1-2%, in order to provide for adequate emulsification of the flavor oil. It has surprisingly been found that the addition of as little as about 0.1% anionic emulsifier employed in conjunction with the nonionic provides for a substantial reduction in the amount of nonionic ordinarily needed when employed alone. For example, whereas 1% nonionic by itself will not adequately emulsify the flavor oil, when combined with about 0.1%, preferably about 0.2% anionic, more than suitable emulsification takes place.

Another complex area relating to the formulation of a baking soda mouthwash relates to the amount, type and purity of the water employed and to the water:alcohol ratio, where alcohol is employed in the formulation.

Customarily deionized water is employed in mouthwash formulations. This type of water generally has what is termed an acceptable bacterial count of 100 to 10,000 per ml, which includes non-living bacteria; the water is ordinarily passed through a 1-5 micron filter in order to achieve this result. In the formulation of the instant mouthwash, it has been found that customarily acceptable deionized water is not suitable in forming the product. A product as is herein contemplated when formulated with deionized water often suffers from the drawback that certain insoluble colloidal inorganic materials found as trace impurities even in U.S.P. grade baking soda, interact with the bacteria which were not filtered out, albeit non-living, causing or accelerating the precipitation of baking soda or other colloidal insoluble inorganics and causing a visible sediment.

Furthermore, notwithstanding the flavor compensation referred to above and the fact that U.S.P. grade baking soda is employed, there is still in certain instances a more than acceptable salty taste that a significant segment of the population objects to and therefore one embodiment of the invention eliminates this problem. This problem is believed caused by certain colloidal insoluble inorganics which have been shown to affect the taste of the product by exhibiting bitterness or other negative associated tastes.

It has, therefore, been unexpectedly found that by employing an aqueous solution of baking soda wherein the bacterial concentration is less than about 10 counts/ml obviates these problems. This can be accomplished by filtering an aqueous solution of deionized water and baking soda through a fine micron filter having an opening of about 0.01 to about 1.0 microns, preferably about .5 microns or less, i.e., 0.15 to 0.45 microns, 0.2 to 0.25. The filtration is preferably carried out at least about 12 hours after making the aqueous solution of baking soda, about 12-24 house thereafter.

Suitable filters include, for example, the zeta plus filter media (AMF Cuno) which operates mechanically and by electrokinetic adoption as well as filtering the solution through materials such as celites and the like; and combinations of both systems. Alternatively, the filtration may also be accomplished by filtering the finished product, which contains all of the ingredients.

Baking soda, as stated earlier, is relatively insoluble in an alcohol-water system, and almost completely insoluble in alcohol. The very nature of a mouthwash, however, requires that there be water present, and often, alcohol as well. It has been found that as the level of alcohol in the mouthwash is increased, the level of baking soda susceptible to remaining in solution decreases. Herein a balance has been struck between maintaining a fairly high level of baking soda in solution, and the formulator's desire to incorporate alcohol in the mouthwash both for its antiseptic value and its ability to impart a degree of bite to the formulation.

A side advantage of the alcohol is its ability to lower the freezing point of the water, thereby substantially lessening the possibility of baking soda coming out of solution at reduced temperatures, such as upon storage and when in transit.

A further problem encountered relates to the actual manipulative steps involved in manufacturing the formulation. It has been found necessary to first solubilize the baking soda in the required amount of water and thereafter add thereto a mixture of alcohol containing all of the other ingredients solubilized therein, or vice versa, and most preferably, thereafter filtering the same as aforesaid to achieve the 10 counts/ml.

One of the considerations in formulating a mouthwash is to provide a comfortable feeling in the mouth during use. Advantageously, a suitable mouthwash product should have a low enough viscosity to permit the user to readily manipulate and swish it around in his mouth to effectively gargle. Accordingly, the viscosity of a suitable product in accordance with this invention should be well below 1000 cps preferably less than about 100 cps at room temperature, e.g., about 1.0 to about 10.0 cps.

The particular materials employed in formulating the product are as follows:

The baking soda is U.S.P. grade powdered or granular, respectively, one or more or a variety of particle sizes may be used for example, any distribution as follows, in which percentages represent the cumulative percent retained on the named sieve, and sieve sizes are U.S. Standard: #42 sieve, trace; #100 sieve, 15%; #170 sieve, 20%; #200 sieve, 35%; #325 sieve, 70%; another grade #42, trace; #65, 27%, #80, 60.5%; #100, 92.5%; #170, 99%; #200, 99.7%; and #325, 99.8%. It is to be understood, however, that other grades of baking soda can also be employed. The baking soda is included in amounts of about 3-9% by weight, preferably about 3.5-6.5% and most preferably about 4-5%; at which levels there is principally a saturated solution.

The mouthwash composition according to the invention typically contains about 60 to about 95%, preferably about 70 to 80%, e.g., about 75% by weight water, and 0 to about 20%, preferably about 5 to 15%, e.g., about 8-12% by weight, of a non-toxic cosmetic alcohol such as isopropanol or ethanol. The alcohol component of the mouthwash preferably utilizes as a denaturing component, one of the instant flavor oils.

The flavor oils which are one specific aspect of the invention fall into three classes known as herbal, medicinal and mint. These flavor oils are exemplified by the following materials: anise oil, basil, bay oil, bitter almond oil, boric acid, camphor, cedar leaf oil, chervil, coriander, citronella oil, clove oil, eucalyptus oil, fennel, geranium, lavendar oil, marjoram, menthol, myrrh, mustard oil, orange oil, oregano, parsley, penny-royal, peppermint oil, oil of phenol, pine needle oil, rosemary oil, sage, spearmint oil, tarragon, thyme oil, tolubalsam, oil of terpentine, wintergreen oil, and suitable mixtures thereof. The flavor oil is typically present in an amount of about 0.05-0.4%, by weight, preferably about 0.1-0.3%, more preferably about 0.15-0.25% of the total content of the mouthwash.

A further aspect of the invention relates to the types of dye or color and amount thereof needed. It has been found that the following dyes are eminently suitable, whereas others are not.

Acid Dyes

F.D.& C Blue #1
F.D.& C Red #4
F.D.& C Green #3
D & C Red #3
D & C Red #33
F.D.& C Red #40
F.D.& C Yellow #5

Nonionic Dye

D & C Red #19

The dyes are included in amounts of at least about 0.5% of a 0.1% solution of dye based on the weight of the total mouthwash. More particularly, they are included in amounts of about 0.0005 to 0.002%, most preferably about 0.0005 to 0.0015% by weight, based on the weight of the mouthwash.

In another specific aspect, the invention provides a nonionic surfactant ingredient that effectively emulsifies the flavor oil component in an aqueous mouthwash resulting in a stable formulation. According to this aspect of the invention, the surfactant ingredient is chosen from the group known as nonionic surface active agents, particularly the condensates of sorbitan monostearate with approximately 20 moles of ethylene oxide, condensates of ethylene oxide with propylene oxide, condensates of propylene glycol ("Pluronics") and certain suitable cationic surface-active germicides and antibacterial compounds such as di-isobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxethylene groups attached to the nitrogen (typically containing a total of from about 2 to 50 ethenoxy groups per molecule) and salts thereof with acids, and compounds of the structure

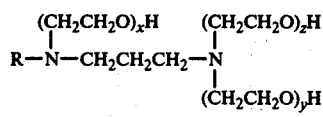

wherein R is a fatty alkyl group containing from about 12 to 18 carbon atoms, and x, y and z total three or higher, as well as salts thereof with mineral or organic acids.

Other suitable nonionic emulsifiers are the condensation products of an α-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant emulsifiers are heteric polymers having a molecular weight in the range of 400 to about 1600 and containing 40% to 80% by weight of ethylene oxide, with an α-olefin oxide to polyhydric alcohol mole ratio in the range of about 1:1 to 1:3. These emulsifiers are manufactured using well-known polymerization techniques under conditions of high temperature and high pressure. These nonionic emulsifiers may be mixed with similar nonionics as well as other types of nonionics described herein.

It is preferred to employ about 0.5 to 4.0% by weight nonionic, preferably about 0.75 to 3.0%, and more preferably about 1.5 to 2.5%.

It is preferable to employ at least a minor amount of an anionic surfactant in conjunction with one or more of the above-mentioned nonionics, or in total replacement therefor.

Suitable anionic surfactants include the water-soluble salts of higher fatty acid monosulfates, such as water-soluble salts of compounds having long chain alkyl radicals, i.e., the sodium salt of the monosulfated monoglyceride of hydrogenated coconut oil fatty acids, $C_{10-18}$ fatty acid monoglyceride sulfates, higher alkyl sulfates, such as sodium laurylsulfate, alkyllauryl sulfonates such as sodium dodecylbenzene sulfonate, olefin sulfonates, such as sodium olefin sulfonate in which the olefin group contains 12-21 carbon atoms, higher alkyl sulfoacetates, higher fatty acid ester of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last-mentioned amides are N-lauryl sarcosine, and the sodium, potassium, and ethanolamine salts of N-lauroyl, N-myristoyl or N-palmitoyl sarcosinates, which should be substantially free from soap or similar higher fatty acid material which tends to substantially reduce the effect of these compounds.

The olefin sulfonates referred to above typically are a long chain of alkenyl sulfonates.

The α-olefin feedstock preferably contains olefins of 8-25 carbon atoms, most preferably 12-21 carbon atoms. The feedstock may contain minor amounts of other constituents, such as secondary or internal olefins, diolefins, cyclic olefins, aromatics, napthalenes, and alkanes. Best results have been obtained when α-olefins (where $R_1$ is H) constitute a major proportion, for example, about 70% and preferably at least 90% of the feedstock. A particularly preferred olefin feedstock contains in the range of about 12 to 21 carbon atoms in the molecule and yields olefin sulfonates having excellent detergency properties. Especially good foaming characteristics have been obtained by the use of a feedstock whose alpha-olefin content consists essentially of compounds of 15 to 18 carbon atoms.

The above materials typically contain at least about 50% by weight of long-chain alkenyl sulfonate, up to about 33% by weight of hydroxy alkane sulfonate, and up to about 15% of impurities, such as long-chain water-insoluble sultones, most of which impurities are characterized as being soluble in acetone.

The olefin sulfonate is generally employed in the form of its sodium salt. It is within the scope of this invention to use other water-soluble salts, for example, salts of other alkali metals such as potassium salts of alkaline earth metals, such as magnesium and calcium, triethanolamine, salts and the like, as well as mixtures of a salt such as a sodium salt with the free olefin sulfonic acid.

Where the anionic component is employed in conjunction with the nonionic, the former may be included in substitution in any corresponding amount, or in amounts as little as about 0.01% up to about 0.5%. As little as about 0.05% anionic reduces the amount of nonionics from 2.0% to 1.0%, thereby causing a 50% reduction in nonionic required. Increasing amounts of anionic produce correspondingly lesser amounts of nonionic needed in the formulation. Where desired, the nonionic can be completely replaced by the anionic emulsifier, which may be included in amounts of about 0.05 to 0.2% by weight, preferably about 0.075 to 0.15%.

The mouthwash composition preferably contains glycerine in amounts of about 1 to 15 percent by weight, with compositions containing between about 8 to 12 percent having particularly desirable characteristics. The glycerine functions as a sweetener, supplies "body" to the compositions and a "velvety" feel in the mouth. It may be replaced in whole or in part by such equivalent materials as sorbitol or propylene glycol or other suitable polyol humectants.

Pursuant to the invention, the pH of the mouthwash formulation is about 8.0 to about 9.3, preferably about 8.5.

The mouthwash composition can be prepared by combining the specified amount of baking soda in an amount of treated water sufficient to bring the total of all the components to 100 percent. It is preferable to admix the alcohol-soluble components in the alcohol in a suitable mixing vessel and then add the aqueous baking soda solution to the vessel, or vice versa. Where alcohol is not included in the formulation, the ingredients ordinarily admixed with the alcohol will be admixed with the sodium bicarbonate solution.

The filtration step is carried out in accordance with generally acceptable filtration procedures as are known in the art, such as, for example, the procedure known as cold sterilization, i.e., passing the liquid at room temperature through a filter as aforesaid, either the aqueous solution of baking soda or the finished mouthwash formulation as detailed hereinbefore.

EXAMPLE 1

A mouthwash including the following ingredients is formulated:

| | Percent by Weight |
|---|---|
| Denatured ethanol (95%) | 9.80 |
| Polyoxypropylene polyoxyethylene Condensate ("Pluronic" F-108) (Nonionic emulsifier) | 2.00 |
| Mixed mint (methol, spearmint, peppermint) Flavor oil | 0.20 |
| Glycerine | 10.00 |
| Sodium saccharine | 0.03 |
| FD&C Green #3 (0.1% solution) | 0.50 |
| FD&C Yellow #5 (0.1% solution) | 1.30 |
| NaHCO$_3$ | 5.00 |

-continued

| | Percent by Weight |
|---|---|
| Deionized water | q.s. |
| | 100.00 |

The product is prepared by first solubilizing the sodium bicarbonate in water. The solution of bicarbonate is allowed to stand for about 24 hours whereupon it is filtered by passing the same through a fine filter having an opening of about 0.22 microns (such as Zeta plus filter media). Into a separate vessel, the remainder of the ingredients are mixed with the alcohol. The filtered solution of sodium bicarbonate is then admixed with the alcoholic system. This formulation is visually clear with a green tint, does not separate during storage and has a refreshing taste and a pH of about 8.5.

EXAMPLE 2

The formulation of Example 1 is repeated with the substitution of D & C Red #19 for the dye system of Example 1.

This formulation is prepared in the same manner with the exception that the bicarbonate solution is not first filtered, but is combined with the alcoholic system, the mouthwash product is then permitted to stand for about 24 hours whereupon it is passed through a filter having an opening of about 0.22 microns.

EXAMPLE 3

The formulation of Example 1 is repeated with the exception that polyoxyethylene 20 sorbitan monoisostearate (POE20) is substituted for the "Pluronic" F-108. The making procedure is the same as in Example 1 except that the sodium bicarbonate solution is passed through a filter having an opening of about 0.45 microns.

EXAMPLE 4

The formulation of Example 2 is repeated with the exception that 0.2% sodium lauryl sulfate is substituted for 1.0% of the "Pluronic" F-108. The making procedure is the same except that a 0.45 micron filter is employed.

EXAMPLE 5

The formulation of Example 1 is repeated as is the making procedure, with the exception that the bicarbonate solution if filtered after standing for about 12 hours.

EXAMPLE 6

The formulation of Example 2 is repeated with the exception that the mouthwash product is filtered after standing for about 12 hours.

EXAMPLE 7

A mouthwash having the following formulation is prepared in accordance with the procedure of Example 1.

| | Percent by Weight |
|---|---|
| Denatured alcohol (95%) | 12.00 |
| Sodium lauryl sulfate (Anionic emulsifier) | 0.2 |
| Combination (peppermint, menthol, spearmint and anethol) Flavor oil | 0.20 |

-continued

| | Percent by Weight |
|---|---|
| Glycerine | 10.00 |
| Sodium saccharine | 0.04 |
| Color (FD&C blue #1; 0,1% solution) | 0.60 |
| NaHCO$_3$ | 4.00 |
| Deionized water | q.s. |

EXAMPLE 8-13

The following mouthwashes having varying intensities are formulated following the making procedure of Example 1 or 2 as indicated

| Ingredient | Example Number; Percent by Weight | | | | | |
|---|---|---|---|---|---|---|
| | 8[6] | 9[7] | 10[7] | 11[6] | 12[6] | 13[7] |
| Denatured alcohol (95%)[1] | — | — | 10.0 | 15.0 | 12.0 | 8.0 |
| Emulsifier nonionic | 2.0[3] | 1.00[2] | 1.5[3] | 0.5[2] | 2.00[3] | 0.00 |
| Flavor oil of Example 1 | 0.1 | 0.20 | 0.2 | 1.0 | 0.10 | 0.20 |
| Glycerine[4] | — | — | 10.0 | 15.0 | — | 15.00 |
| Sweetener[5] | — | — | — | 0.1 | 0.06 | 0.10 |
| NaHCO$_3$ | 8.0 | 7.0 | 5.0 | 3.0 | 4.0 | 6.0 |
| Sodium lauryl sulfate (Emulsifier Anionic) | — | — | — | 0.1 | — | 0.2 |
| Deionized water | q.s. | q.s. | q.s. | q.s. | q.s. | q.s. |

[1] Ethanol or isopropanol
[2] Pluronic F-108
[3] PO E-20
[4] Sorbitol or propylene glycol can be substituted for glycerine
[5] Sodium saccharine
[6] Example 1 procedure
[7] Example 2 procedure In Examples 8 and 9, where alcohol is not present, the remaining ingredients are admixed with the aqueous solution of sodium bicarbonate.

Although the present invention has been described with reference to particular embodiments and examples, it will be apparent to those skilled in the art that variations and modifications of this invention can be made and that equivalents can be substituted therefor without departing from the principles and true spirit of the invention.

I claim:

1. A stable mouthwash product having a pH of about 8.0 to about 9.3 and comprising approximately by weight 3 to 9% of sodium bicarbonate, 0.005 to 0.002% of a dye selected from the group consisting of F.D. & C. Blue #1, Red #4, Green #3, Red #40, Yellow #5, D.&C. Red #3, Red #19 and Red #33, 5 to 15% of ethanol or isopropanol, 0.05 to 0.4% of a herbal, medicinal or mint flavor oil, 0.01 to 4.0% of at least one member of the group consisting of nonionic and anionic emulsifiers for the flavor oil, and the balance deionized water, said product being prepared by solubilizing the sodium bicarbonate in deionized water, mixing the resulting solution with a solution of the remaining components in the ethanol or isopropanol, and filtering the sodium bicarbonate solution through a 0.1–1.0 micron filter at least about 12 hours after the formation thereof whereby said product has a bacterial concentration of less than 10 counts/mol.

2. The product as defined in claim 1 containing a mixture of said nonionic and anionic emulsifiers.

3. The product as defined in claim 1 wherein said emulsifier is a nonionic.

4. The product as defined in claim 1 wherein said emulsifier is anionic.

5. The product as defined in claim 1 wherein the ratio of said emulsifier to said flavor oil is about 1:1 to 10:1.

6. The product as defined in claim 1 further containing about 1 to 15% humectant.

7. The product as defined in claim 1 having a viscosity at room temperature of about 1.0 cps to about 10.0 cps.

* * * * *

UNITED STATES PATENT AND TRADEMARK OFFICE
CERTIFICATE OF CORRECTION

PATENT NO. : 4,132,770
DATED : JANUARY 2, 1979
INVENTOR(S) : JORDAN BARTH

It is certified that error appears in the above-identified patent and that said Letters Patent are hereby corrected as shown below:

COLUMN 10, LINE 7 (CLAIM 1, LINE 3),

CANCEL "0.005" AND INSERT --0.0005--.

Signed and Sealed this

Twenty-second Day of April 1980

[SEAL]

Attest:

SIDNEY A. DIAMOND

Attesting Officer     Commissioner of Patents and Trademarks